(12) United States Patent
Yoo et al.

(10) Patent No.: US 9,512,453 B2
(45) Date of Patent: Dec. 6, 2016

(54) METHOD FOR PREPARING NOVEL PROCESSED GINSENG OR AN EXTRACT THEREOF, THE USUALLY MINUTE GINSENOSIDE CONTENT OF WHICH IS INCREASED

(75) Inventors: Young-Hyo Yoo, Seoul (KR); Sun-Ok Kim, Seoul (KR); Jung Hyo Choi, Yongin-si (KR); Soo-Hyun Bae, Seoul (KR); Sun Kyu Park, Seoul (KR); Jeom Yong Kim, Seoul (KR)

(73) Assignee: GREEN CROSS WELLBEING CORPORATION, Seongnam-Si, Gyeonggi-Do (KR)

( * ) Notice: Subject to any disclaimer, the term of this patent is extended or adjusted under 35 U.S.C. 154(b) by 864 days.

(21) Appl. No.: 13/698,005

(22) PCT Filed: May 13, 2011

(86) PCT No.: PCT/KR2011/003544
§ 371 (c)(1),
(2), (4) Date: Feb. 1, 2013

(87) PCT Pub. No.: WO2011/142618
PCT Pub. Date: Nov. 17, 2011

(65) Prior Publication Data
US 2013/0122122 A1    May 16, 2013

(30) Foreign Application Priority Data
May 14, 2010 (KR) .................. 10-2010-0045394

(51) Int. Cl.
| A61K 31/513 | (2006.01) |
| C12P 19/14 | (2006.01) |
| A61K 36/258 | (2006.01) |
| A61K 31/282 | (2006.01) |
| A61K 31/519 | (2006.01) |
| A61K 45/06 | (2006.01) |

(52) U.S. Cl.
CPC .............. *C12P 19/14* (2013.01); *A61K 31/282* (2013.01); *A61K 31/513* (2013.01); *A61K 31/519* (2013.01); *A61K 36/258* (2013.01); *A61K 45/06* (2013.01); *A61K 2236/19* (2013.01)

(58) Field of Classification Search
None
See application file for complete search history.

(56) References Cited

U.S. PATENT DOCUMENTS

| 2003/0185910 A1* | 10/2003 | Yun et al. ..................... 424/728 |
| 2004/0028671 A1 | 2/2004 | Jin et al. |
| 2005/0031711 A1 | 2/2005 | Park |
| 2012/0149656 A1 | 6/2012 | Fu et al. |

FOREIGN PATENT DOCUMENTS

| CN | 1477205 A | 2/2004 |
| JP | 63012300 A | 1/1988 |
| JP | 2003277246 A | 12/1991 |
| JP | 2005009123 A | 1/1993 |
| JP | 2006209773 A | 8/1994 |
| JP | 2008291194 A | 11/1996 |
| JP | 10014523 A | 1/1998 |
| JP | 2010099094 A | 4/1998 |
| JP | 2002348245 A | 12/2002 |
| JP | 2003160497 A | 6/2003 |
| JP | 2004519224 A | 7/2004 |
| JP | 2004537565 A | 12/2004 |
| JP | 2005504799 A | 2/2005 |
| JP | 2006502082 A | 1/2006 |
| JP | 2008100999 A | 5/2008 |
| JP | 2009537572 A | 10/2009 |
| JP | 2010132625 A | 6/2010 |
| KR | 10-2000-0045694 A | 7/2000 |
| KR | 10-2000-0062140 A | 10/2000 |
| KR | 10-2005-0053048 A | 6/2005 |
| KR | 10-2006-0001834 A | 1/2006 |
| KR | 10-2006-0074970 A | 7/2006 |
| KR | 10-0805852 B1 | 2/2008 |
| KR | 100805852 B1 | 2/2008 |
| KR | 10-2009-0037140 A | 4/2009 |
| WO | 03010182 A1 | 2/2003 |
| WO | 03024459 A1 | 3/2003 |
| WO | WO 03086438 A1 * | 10/2003 |
| WO | 2005030235 A1 | 4/2005 |
| WO | 2005034963 A1 | 4/2005 |
| WO | WO 2005034963 A1 * | 4/2005 |
| WO | 2008155998 A1 | 12/2008 |
| WO | 2008155999 A1 | 12/2008 |

OTHER PUBLICATIONS

Slichenmyer et al. Anticancer Drugs. Dec. 1991;2(6):519-530 (Abstract only).*
Supplemental European Search Report Application No. EP 11780835.2, dated Nov. 20, 2013, 9 pages.
Office Action issued in related Chinese Patent Application No. 201180024044.2 dated Nov. 1, 2013, 17 pages.
Official Notice of Preliminary Rejection issued in related Japanese Patent Application No. 2013-50028, dated Dec. 3, 2013, 7 pages.

* cited by examiner

*Primary Examiner* — Amy L Clark
(74) *Attorney, Agent, or Firm* — Rothwell, Figg, Ernst & Manbeck, P.C.

(57) ABSTRACT

A method for preparing a processed ginseng or a processed ginseng extract having increased contents of ginsenosides Rg3 and Rh2 by (a) inoculating an *Aspergillus niger* strain into a medium composed of ginseng and wheat bran; (b) culturing the strain of step (a); (c) purifying the cultured material of step (b) by ultrafiltration; (d) separating an enzyme from the purified material of step (c); (e) adding the enzyme of step (d) to ginseng or red ginseng; (f) fermenting the ginseng or red ginseng of step (e); (g) separating the fermented material of step (f) to obtain a supernatant; (h) concentrating the supernatant of step (g); (i) reacting the concentrate of step (h) with organic acid; and (j) neutralizing, filtering, purifying, concentrating and drying the reaction product of step (i).

6 Claims, 4 Drawing Sheets

METHOD FOR PREPARING NOVEL PROCESSED GINSENG OR AN EXTRACT THEREOF, THE USUALLY MINUTE GINSENOSIDE CONTENT OF WHICH IS INCREASED

CROSS REFERENCE TO RELATED APPLICATIONS

This application is a 35 U.S.C. §371 National Phase Entry Application from PCT/KR2011/003544, filed May 13, 2011, and designating the United States, which claims priority under 35 U.S.C. §119 to Korean Patent Application No. 10-2010-0045394 filed May 14, 2010, which is incorporated herein in its entirety.

TECHNICAL FIELD

The present invention relates to a method of preparing a novel processed ginseng or processed ginseng extract having increased ginsenoside contents by preparing saponinase, fermenting ginseng or red ginseng with the prepared saponinase and hydrolyzing the fermented ginseng or red ginseng with an organic acid and to an anticancer supplement composition comprising the processed ginseng or processed ginseng extract prepared thereby.

BACKGROUND ART

In plant taxonomy, ginseng is a perennial plant belonging to the genus *Panax* of the family Araliaceae, and about 11 species of ginseng are known so far. Among them, *Panax* Ginseng C. A. Meyer is typically known to have excellent medicinal effects. The term "ginseng" is used in the broadest sense to include all fresh ginseng, white ginseng, red ginseng, wild mountain ginseng, woods grown ginseng, tail ginseng, cultured ginseng and the like. Ginseng is a natural material that has been used as a highly valuable medicinal drug in Chinese medicine, and the medicinal effects of ginseng are found in many medical books. Although ginseng has been used for a long period of time, the scientific elucidation of effects of ginseng by clinical studies is still insufficient. Nevertheless, even after modern medicine was introduced, ginseng did not lose its popularity and ranks first among health functional foods. This is thought to be because ginseng is a crude drug that exhibits clinically proven medicinal effects, has fewer side effects and is highly safe. The major functional components of ginseng are ginseng saponins which are distinguished from the saponins of other plants and called ginsenosides. The ginseng saponins have pharmacological effects, including anticancer, anti-allergy, anti-inflammation, central nervous inhibition, relaxation, pain relief, memory improvement, liver injury recovery, protein and lipid synthesis stimulation, anti-diabetes, anti-stress, antioxidant substance promotion stimulation, immune regulation, platelet aggregation inhibition and anti-aging effects.

Saponins are classified into a variety of ginsenosides according to the kind and number of sugars (glucose, arabinose, and rhamnose) bound to a substituent. These saponins are hardly degraded by digestive enzymes in vivo after oral intake (Hasegawa, H. et al., Microbial Ecololgy in Health and Disease, 12, 85-91, 2000) and absorbed after degradation into 20(S)—O-β-protopanaxadiol 20-O-β-D-glucopyranoside, 20(S)-protopanaxadiol and 20(S)-protopanaxatriol by intestinal microorganisms (Hasegawa, H. et al., Planta Medica, 62, 453-457, 1996). However, the absorption of saponins differs between individuals, because intestinal microorganisms significantly differ between individuals.

Meanwhile, among the main components of ginseng, saponins such as ginsenosides Rb1, Rb2 and Rc are known to exhibit the pharmacological effects of ginseng. However, it is known that the components of ginseng, which are substantially involved in anticancer effects, inhibition of cancer cell metastasis, or anti-allergy effects, are compound K (comp K), and saponins of ginsenosides Rb1, Rb2 and R3, which are contained in very small amounts in ginseng. Ginsenoside Rh2 and compound K, which comprise a glucose molecule bound to a substituent, have excellent anticancer, anti-allergic and anti-inflammatory effects and, at the same time, show high intestinal adsorption and absorption rates, because the number of sugar chain bonds therein is not large so that they have low hydrophilicity. Thus, in order to use the anticancer, anti-allergic and immune-enhancing effects of ginseng, it is preferable to increase the contents of compound K and ginsenosides Rh2, Rh1 and Rg3, which are not contained or are contained in very small amounts in ginseng.

Accordingly, in recent years, in order to increase the contents and facilitate the in vivo absorption of ginseng active ingredients (ginsenosides) which are not contained or are contained in very small amounts, various methods have been attempted, including a method of fermenting ginseng using microorganisms, a method of treating ginseng with enzymes, and a method of hydrolyzing ginseng with acid. For example, Korean Patent Application No. 2000-58997 discloses a method of making absorbable, acid-saccharified ginseng using sulfuric acid or hydrochloric acid, and Korean Patent Laid-Open Publication No. 2003-87250 discloses a method of making processed ginseng having increased contents of ginseng active ingredients and containing red ginseng-specific ginsenosides using ultrahigh pressure. Further, Korean Patent Laid-Open Publication No. 2006-1834 discloses a method of preparing fermented ginseng or fermented red ginseng, comprising a step of inoculating ginseng or red ginseng with Kimchi lactic acid bacteria and treating the inoculated ginseng or red ginseng with acid, and Korean Patent Laid-Open Publication No. 2003-61756 discloses a method for preparing a fermented ginseng solution having excellent functional and sensory properties, the method comprising fermenting ginseng with *Aspergillus* and degrading the fermented ginseng with amylase and protease. In addition, Korean Patent Laid-Open Publication No. 2006-74970 discloses a fermented ginseng comprising a substance obtained by degrading glycosides in ginseng with *Lactobacillus casei* strain Hasegawa, and Korean Patent Laid-Open Publication No. 1998-40224 discloses a fermented ginseng comprising degraded saponin products obtained by fermenting ginseng with various *Lactobacillus* strains.

DETAILED DESCRIPTION OF THE INVENTION

Technical Problem

As described above, in order to increase the contents and facilitate the in vivo absorption of ginseng ginsenosides which are not contained or are contained in very small amounts, various methods have been attempted, including a method of fermenting ginseng using microorganisms, a method of treating ginseng with enzymes, and a method of hydrolyzing ginseng with acid. However, a high-value-added ginseng product has not yet been developed or produced. Specifically, when producing large amounts of ginseng products using high energy in order to enhance specific components, there are problems associated with efficiency, and when fermenting ginseng with various microorganisms, there is a problem in that the contents of standard active ingredients cannot be controlled at constant levels.

Therefore, it is an object of the present invention to change the ginsenoside composition of ginseng.

Another object of the present invention is to increase the contents of Rg3 and Rh2 among the ginsenosides of ginseng.

Still another object of the present invention is to provide a method for effectively extracting active ingredients from ginseng.

Yet another object of the present invention is to provide a ginseng extract having high ginsenoside contents, preferably high Rg3 and Rh2 contents, and an anticancer supplement composition comprising the ginseng extract.

Technical Solution

To achieve the above objects, in accordance with one aspect, the present invention provides a method for preparing a processed ginseng or a processed ginseng extract, the method comprising the steps of:

(a) inoculating an *Aspergillus niger* strain into a medium composed of ginseng and wheat bran; (b) culturing the strain of step (a); (c) purifying the cultured material of step (b); (d) separating an enzyme from the purified material of step (c); (e) adding the enzyme of step (d) to ginseng or red ginseng; (f) fermenting the ginseng or red ginseng of step (e); (g) separating the fermented material of step (f) to obtain a supernatant; (h) concentrating the supernatant of step (g); (i) reacting the concentrate of step (h) with organic acid; and (j) neutralizing, filtering, purifying, concentrating and drying the reaction product of step (i).

In accordance with another aspect, the present invention provides a method for preparing a processed ginseng or processed ginseng extract having increased ginsenoside contents, preferably increased Rg3 and Rh2 contents, the method comprising the steps of:

(a) inoculating an *Aspergillus niger* strain into a medium composed of ginseng and wheat bran; (b) culturing the strain of step (a); (c) purifying the cultured material of step (b); (d) separating an enzyme from the purified material of step (c); (e) adding the enzyme of step (d) to ginseng or red ginseng; (f) fermenting the ginseng or red ginseng of step (e); (g) separating the fermented material of step (f) to obtain a supernatant; (h) concentrating the supernatant of step (g); (i) reacting the concentrate of step (h) with organic acid; and (j) neutralizing, filtering, purifying, concentrating and drying the reaction product of step (i).

The origins of the ginseng that is used in the inventive method for preparing the processed ginseng or the processed ginseng extract include, but are not specifically limited to, Korea, USA, Japan, Himalaya, Vietnam and China. In the case of the red ginseng, a red ginseng slender tail and a red ginseng root may be used in the present invention.

The form of the ginseng that is used in the preparation of the processed ginseng or the processed ginseng extract according to the present invention may be ginseng, red ginseng, ginseng or red ginseng extract powder, or a ginseng or red ginseng extract. The extract may be prepared by hot-water extraction, alcohol extraction or a combination thereof. The particle size of the ginseng or red ginseng extract powder is not specifically limited and may be, for example, about 30-150 mesh. The extract may be prepared by vacuum distillation or thin-film distillation.

Further, the ginseng that is used in the present invention may be selected from among ginseng roots, leaves and stems, and the red ginseng that is used in the present invention may be selected from among red ginseng slender tails and red ginseng roots.

Hereinafter, the present invention will be described in detail.

The stain that is used in step (a) of the preparation method of the present invention is *Aspergillus niger* (ACTC6985) obtained from the Biological Resource Center. The medium in step (a) comprises ginseng powder and wheat bran, which are maintained at a weight ratio (g/g) of 1:1-1:5, preferably 1:3, and it is inoculated with *Aspergillus niger*. Inoculation of the medium with *Aspergillus niger* is performed such that the number of spores in an *Aspergillus niger* spore suspension is $5 \times 10^5$ spores per g of the medium and the initial water content is maintained at 50-80%, preferably 65%.

In step (b), the culture temperature is maintained at 2~40° C., preferably 30° C., and when the strain is cultured for 3-7 days, the production of saponinase (saponin degrading enzyme) reaches the highest level.

In steps (c) and (d), 0.02M sodium acetate buffer solution is added to the medium after completion of the strain, after which the medium was filtered through a Watman glass microfiber filter, and then further filtered through a 0.22 μm bottle top filter containing an enzyme in order to completely remove the spores. The collected filtrate is passed through an ultrafiltration membrane having a cutoff molecular weight of 100 KDa to obtain a purified enzyme solution. Ginseng or red ginseng may be fermented with the concentrated purified saponinase solution obtained as described above. Alternatively, alcohol may be added to the purified enzyme solution to separate saponinase. Specifically, alcohol may be added to the purified saponinase solution to precipitate protein, thereby obtaining saponinase as a mass, or the saponinase solution may be freeze-dried to obtain saponinase powder.

In steps (e) and (f), the saponinase is added to ginseng or red ginseng powder or a ginseng or red ginseng extract or concentrate powder in an amount of 5-20% of the weight of the ginseng or red ginseng powder or the ginseng or red ginseng extract or concentrate powder, and then cultured at a suitable fermentation temperature of 25~60° C., preferably 30~35° C., for 6-24 hours. Preferably, 50 g of the enzyme is added to a suspension of 1 kg of the ginseng or red ginseng extract in 30 L of water.

In step (g), alcohol is added to the fermented ginseng or red ginseng to precipitate the saponinase, and the supernatant is separated by filtration (0.8 μm filter paper) or centrifugation, and the supernatant is collected and concentrated at 50° C.

In step (i), an organic acid is added to the fermented ginseng or red ginseng and is reacted at 40~80° C. for 2-18 hours. Examples of the organic acid that is used in step (i) include, but are not specifically limited to, acetic acid, lactic acid, citric acid, malic acid, tartaric acid, and mixtures thereof. The organic acid is added to a 10% solution of the concentrate of step (h) in purified water in an amount of 1-50 wt %, preferably 5-25 wt %, based on the weight of the concentrate solution.

In steps (h) and (j), water or an acid neutralizing agent that is a food additive may be used to neutralize the product of the reaction with the organic acid. The concentration of the product of the reaction with the organic acid may be performed at 50° C. The concentration of the reaction product may be performed after adding water or alcohol to the reaction product, filtering the mixture. Alternatively, the concentration of the reaction product may be performed after purifying the organic acid reaction product with resin or a solvent fraction, such as butanol or ethyl acetate, according to a general purification process.

In addition, when the processed ginseng or processed ginseng extract having increased contents of ginsenosides Rg3 and Rh2, prepared by the method of the present invention, is used in combination with an anticancer agent which has been clinically used, it exhibits a synergistic anticancer effect and provides a pharmaceutical composition or anticancer supplement agent for preventing and treating toxicity in bone marrow, blood cells, the liver or the kidneys, which is caused by the anticancer agent. Examples of the anticancer agent include cisplatin, carboplatin, paraplatin, oxaliplatin, nedaplatin, doxorubicin, taxol, tamoxifen, camtobell, adrucil, glivec, etoposide, zometa, oncovin, lupron, gemzar, 5-fluorouracil, leucovorine, irinotecan and the like.

The processed ginseng or processed ginseng extract having increased contents of ginsenosides Rg3 and Rh2, prepared by the method of the present invention, is preferably used in an amount of 0.1-1000 parts by weight based on 1 part by weight of the anticancer agent. If the processed ginseng or the processed ginseng extract is used in an amount in the above range, it can increase the anticancer effect of the anticancer agent and can effectively reduce toxicity caused by the anticancer agent.

Advantageous Effects

The use of the preparation method according to the present invention can provide a processed ginseng or processed ginseng extract having significantly increased ginsenoside contents.

The use of the preparation method according to the present invention can provide a processed ginseng or processed ginseng extract having increased contents of ginsenosides, particularly Rg3 and Rh2.

In the present invention, the contents of ginsenosides Rg3 and Rh2 were compared between a ginseng fermented only with saponinase, a processed ginseng subjected to an organic acid process, and a processed ginseng prepared by the method of the present invention. As a result, it could be seen that the contents of ginsenosides Rg3 and Rh2 were significantly higher in the processed ginseng, subjected to both the saponinase process and the organic acid process, than in the processed ginseng subjected to only the saponinase process or the organic acid process (Table 1).

Meanwhile, the saponinase is an enzyme obtained by culturing *Aspergillus niger* in a medium comprising ginseng and wheat bran, and this technology is already described in, for example, Korean Patent Laid-Open Publication No. 10-1999-45180 relating to a method of preparing a ginseng saponin by changing the sugar chain of ginseng saponin with an enzyme. In addition, it is known that mold has high activities of β-glucosidase, α-arabinosidase and α-rhamnosidase and secretes enzymes such as protease and cellulose, which are helpful in fermentation of ginseng or red ginseng. However, the prior technologies have a shortcoming in that, when ginseng or red ginseng is fermented, the ginsenoside components are not constantly changed so that the fermented ginsenoside components are not constantly produced.

In the present invention, it was found that an enzyme obtained by ultrafiltration after culture of *Aspergillus niger* has β-glucosidase and α-rhamnosidase. Also, it was found that the obtained enzyme is composed of β-glucosidase and α-rhamnosidase mixed at a weight ratio (g/g) of 3:1 to 8:1 and has an enzymatic activity which is at least two times higher than that before ultrafiltration. The activities of enzyme 1 passed through an ultrafiltration membrane and enzyme 2 not passed through an ultrafiltration membrane were examined by TLC. As a result, it was confirmed that the enzyme passed through the ultrafiltration membrane produced F2 which was converted to Rh2 by reaction with an organic acid, but the enzyme not passed through the ultrafiltration membrane produced a larger amount of compound K (Com K) so that the amount of F2 converted to Rh2 was small (FIG. 4). Based on this finding, the present invention has been completed. Specifically, in the present invention, the activity of an enzyme is increased by a method of purifying an enzyme capable of expressing a high level of ginsenoside Rh2 from a mixed enzyme expressed in *Aspergillus niger*, and a standardized processed ginseng or processed ginseng extract having increased contents of ginsenoside components can be produced using saponinases having a constant ratio of β-glucosidase and α-rhamnosidase. Thus, the present invention provides a standardized preparation method, which can increase the contents of ginsenosides Rg3 and Rh2 and can prepare a processed ginseng or processed ginseng extract containing constant amounts of Rg3 and Rh2. Thus, the present invention can prepare a processed ginseng or red ginseng having increased contents of Rg3 and Rh2 while solving the prior art problem in that the ratio of the change in ginsenoside contents during fermentation could not be predicted.

In addition, when each purified saponinase is used, there is a problem in that large amounts of time and cost are required for enzyme purification. However, according to the present invention, the production of saponinases having a constant ratio is possible and the process of purifying saponinases is simple and convenient, and thus mass production is easy and purification yield is high so that production cost can be reduced. Moreover, when fermentation is carried out using a mixture of various microorganisms, there is a problem of cross-contamination with other microorganisms. However, cross-contamination can be prevented using the single mold *Aspergillus niger*.

In addition, according to the present invention, in order to ferment ginseng or red ginseng, saponinases are produced. Using the produced saponinases, ginseng or red ginseng is fermented, and then an organic acid is added to hydrolyze the fermented ginseng or red ginseng. As the prior art related thereto, Korean Patent Application No. 10-2005-94311 discloses a method of preparing a fermented ginseng or red ginseng using Kimchi lactic acid bacteria. According to this prior method, ginseng or red ginseng is fermented with Kimchi lactic acid bacteria and treated with Kimchi lactic acid bacteria, thereby preparing a fermented ginseng or red ginseng. However, it could be seen that the fermented ginseng or red ginseng prepared according to this prior art contains little or no Rh2 and contains a small amount of Rg3 (FIGS. 5 and 6).

In order to solve these problems, in the present invention, saponinases purified by ultrafiltration are used to ferment ginseng or red ginseng, and an organic acid is added, thereby preparing a processed ginseng or red ginseng having increased contents of Rg3 and Rh2.

Preferably, in a processed ginseng or processed ginseng extract according to the present invention, the contents of ginsenosides Rg3 and Rh2 are 0.05-1%, and in a processed ginseng extract prepared using a ginseng concentrate or red ginseng concentrate, the contents of ginsenosides Rg3 and Rh2 are 0.5-5%. Moreover, in a processed ginseng extract prepared using ginseng concentrate powder or red ginseng concentrate powder, the contents of ginsenosides Rg3 and Rh2 are 0.5-30%, and in a processed ginseng extract prepared by purifying ginseng saponins or red ginseng saponins, the contents of ginsenosides Rg3 and Rh2 are 30-50%.

In addition, when the processed ginseng or processed ginseng extract having increased contents of Rg3 and Rh2, prepared by the method of the present invention, is used in combination with an anticancer agent which has been clinically used, it exhibits a synergistic anticancer effect and prevents toxic in bone marrow, blood cells, the liver or the kidneys, which is caused by the anticancer agent.

BRIEF DESCRIPTION OF THE DRAWINGS

FIG. 4 shows that the enzyme passed through the ultrafiltration membrane produced F2 which was converted to Rh2 by reaction with an organic acid, but the enzyme not passed through the ultrafiltration membrane produced a larger amount of compound K (Com K) so that the amount of F2 converted to Rh2 was small.

MODE FOR CARRYING OUT THE INVENTION

Figure 1:
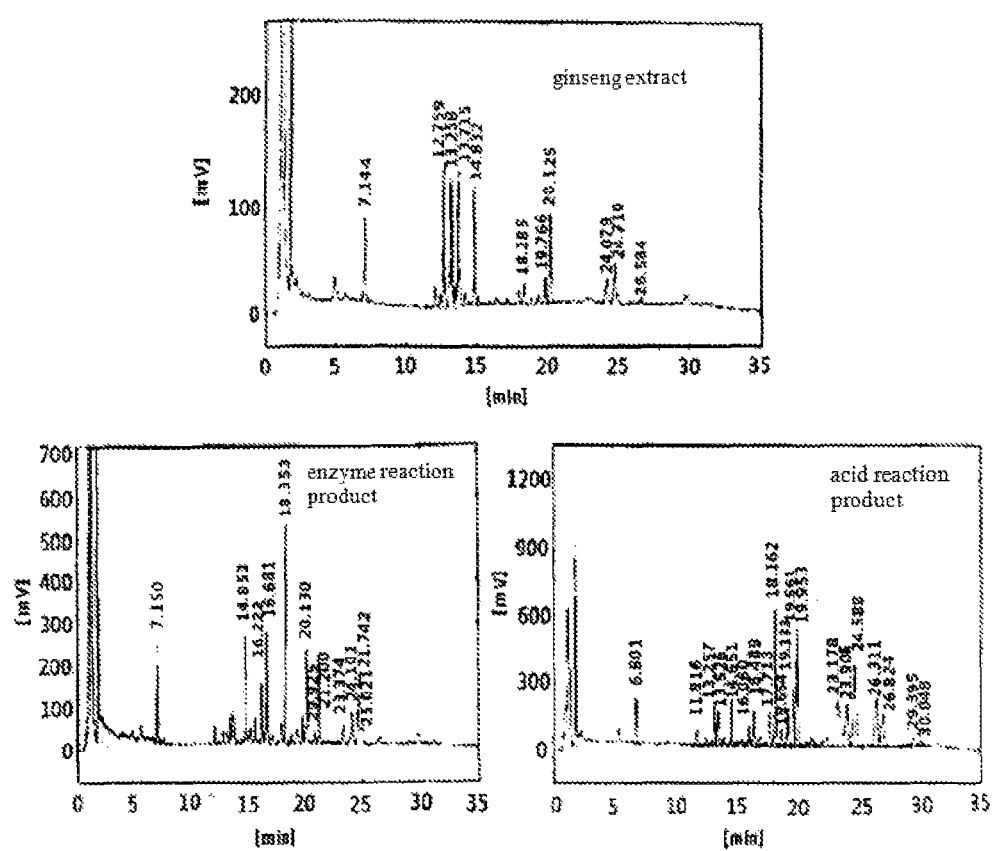
FIG. 1 is a spectrum showing the change in the saponin components of a ginseng extract as a function of an enzyme reactant and an organic acid reactant.

Hereinafter, the present invention will be described in further detail with reference to examples. It is to be understood, however, that these examples are for illustrative purposes only and are not intended to limit the scope of the present invention.

Example 1

Preparation of Processed Ginseng Using Ginseng 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* ($5 \times 10^5$ spores/g of medium) was cultured in the medium at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of ginseng, which was then cultured at 28° C. for 18 hours, after which alcohol was added thereto to precipitate the enzyme, and the supernatant was concentrated. 2 L of purified water was added to 200 g of the concentrate, and 250 g of citric acid was added thereto, and the mixture was stirred at 50° C. for 18 hours. After completion of the reaction, 70% alcohol was added thereto, followed by filtration and concentration, thereby obtaining 200 g of processed ginseng.

Example 2

Preparation of Processed Ginseng Concentrate Using Ginseng Concentrate 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* ($5 \times 10^5$ spores/g of medium) was inoculated into the medium and cultured at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of a ginseng concentrate, which was then cultured at 28° C. for 18 hours, after which alcohol was added thereto to precipitate the enzyme, and the supernatant was concentrated. 2 L of purified water was added to 200 g of the concentrate, and 250 g of citric acid was added thereto, and the mixture was stirred at 50° C. for 18 hours. After completion of the reaction, 70% alcohol was added thereto, followed by filtration and concentration, thereby obtaining 190 g of a processed ginseng concentrate.

Example 3

Preparation of Processed Ginseng Concentrate Powder Using Ginseng Concentrate Powder 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* ($5 \times 10^5$ spores/g of medium) was inoculated into the medium and cultured at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of ginseng concentrate powder, which was then cultured at 28° C. for 18 hours, after which alcohol was added thereto to precipitate the enzyme, and the supernatant was concentrated. 2 L of purified water was added to 200 g of the concentrate, and 250 g of acetic acid was added thereto, and the mixture was stirred at 50° C. for 8 hours. After completion of the reaction, 70% alcohol was added thereto, followed by filtration, concentration and drying, thereby obtaining 195 g of processed ginseng concentrate powder.

Example 4

Preparation of Processed Red Ginseng Using Red Ginseng 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* (5×10$^5$ spores/g of medium) was cultured in the medium at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of red ginseng, which was then cultured at 28° C. for 18 hours, after which alcohol was added thereto to precipitate the enzyme, and the supernatant was concentrated. 2 L of purified water was added to 200 g of the concentrate, and 250 g of acetic acid was added thereto, and the mixture was stirred at 50° C. for 18 hours. After completion of the reaction, 70% alcohol was added thereto, followed by filtration, concentration and drying, thereby obtaining 200 g of processed red ginseng.

Example 5

Preparation of Processed Red Ginseng Concentrate Using Red Ginseng Concentrate 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* (5×10$^5$ spores/g of medium) was inoculated into the medium and cultured at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of a red ginseng concentrate, which was then cultured at 28° C. for 18 hours, after which alcohol was added thereto to precipitate the enzyme, and the supernatant was concentrated. 2 L of purified water was added to 200 g of the concentrate, and 250 g of citric acid was added thereto, and the mixture was stirred at 50° C. for 18 hours. After completion of the reaction, 70% alcohol was added thereto, followed by filtration and concentration, thereby obtaining 190 g of a processed red ginseng concentrate.

Example 6

Preparation of Processed Red Ginseng Concentrate Powder Using Red Ginseng Concentrate Powder 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* (5×10$^5$ spores/g of medium) was inoculated into the medium and cultured at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of red ginseng concentrate powder, which was then cultured at 28° C. for 18 hours, after which alcohol was added thereto to precipitate the enzyme, and the supernatant was concentrated. 2 L of purified water was added to 200 g of the concentrate, and 250 g of acetic acid was added thereto, and the mixture was stirred at 50° C. for 8 hours. After completion of the reaction, 70% alcohol was added thereto, followed by filtration, concentration and drying, thereby obtaining 195 g of processed red ginseng concentrate powder.

Example 7

Preparation of Purified Processed Ginseng Extract Using Ginseng Concentrate Powder 250 g of ginseng powder and 750 g of wheat bran were mixed with each other and sterilized in a high-pressure steam sterilizer at 121° C. and 1.5 atm. 2 L of sterilized water was added to the sterilized medium, and then a suspension of *Aspergillus niger* (5×10$^5$ spores/g of medium) was inoculated into the medium and cultured at 28° C. for 7 days. After completion of the culture, 0.02M sodium acetate buffer solution was added to and mixed with the culture and the medium was filtered. The filtered culture was filtered using an ultrafiltration membrane (100 KDa or more) and concentrated, thereby obtaining 60 g of an enzyme solution. 30 g of the enzyme solution was added to 200 g of ginseng concentrate powder, which was then cultured at 28° C. for 18 hours, after which alcohol was added thereto to precipitate the enzyme, and the supernatant was concentrated. 2 L of purified water was added to 200 g of the concentrate, and 250 g of acetic acid was added thereto, and the mixture was stirred at 50° C. for 8 hours. After completion of the reaction, 70% alcohol was added thereto, followed by filtration, concentration and drying, thereby obtaining 195 g of processed ginseng concentrate powder. The processed ginseng concentrate powder was purified using resin, thereby obtaining 10 g of a processed ginseng extract.

Comparative Example 1

Preparation of Processed Ginseng Concentrate Powder Fermented with Only Saponinase Processed ginseng concentrate powder was obtained in the same manner as Example 1, except that the reaction with the organic acid (acetic acid) was not carried out.

Comparative Example 2

Preparation of Processed Ginseng Concentrate Powder that Reacted with Only Organic Acid Processed ginseng concentrate powder was obtained in the same manner as Example 1, except that treatment with the enzyme was not carried out. Specifically, 2 L of purified water was added to 200 g of ginseng concentrate powder, and 250 g of acetic acid was added thereto, and the mixture was stirred at 50° C. for 8 hours. After completion of the reaction, 70% alcohol was added thereto, followed by filtration, concentration and drying, thereby obtaining 195 g of processed ginseng concentrate powder.

Comparative Example 3

Preparation of Processed Ginseng Concentrate Powder that Reacted with Non-Purified Saponinase Processed ginseng concentrate powder was obtained by reaction with the organic reaction in the same manner as Example 3, except that saponinase not purified by ultrafiltration was used.

Changes in the saponin contents of the processed ginseng or processed ginseng extract according to the present invention are shown in Table 1 below.

TABLE 1

Changes in saponin contents of processed ginseng or processed ginseng extract

| | Content (%) | |
|---|---|---|
| | Rg3 | Rh2 |
| Example 1 | 0.2 | 0.3 |
| Example 2 | 3 | 3 |
| Example 3 | 12 | 18 |
| Example 4 | 0.6 | 0.8 |
| Example 5 | 1 | 3 |
| Example 6 | 5 | 10 |
| Example 7 | 20 | 29 |
| Comparative Example 1 | 1 | 0.05 |
| Comparative Example 2 | 5 | — |
| Comparative Example 3 | 1 | 1 |
| Ginseng | <0.01 | <0.01 |
| Ginseng concentrate | <0.5 | <0.01 |
| Ginseng concentrate powder | <0.5 | <0.01 |
| Red ginseng | <0.01 | <0.01 |
| Red ginseng concentrate | <0.5 | <0.01 |
| Red ginseng concentrate powder | <0.5 | <0.01 |

Test Example 1

Analysis of Saponinase

Each of 50 mg of the standard Rg3 sample and 50 mg of the standard Re sample was added to 20 mM of sodium acetate buffer solution, and the saponinase of the present invention was added thereto. Then, each of the mixtures was stirred at a constant temperature of 32° C. for 22 hours. Each of the enzymatic reaction products was separated into layers by adding butanol thereto, and the butanol layer was concentrated and analyzed by HPLC. The HPLC analysis was performed under the following conditions.
 1) Instrument: Shiseido nanospace SI-2
 2) Column: Capcell Pak C18 UG80 4.6×150 mm (5 μm)
 3) Flow rate: 1.00 mL/min
 4) UV wavelength: 203 nm
 5) Column temperature: 40° C.
 6) Injection amount: 20 μL
 7) Mobile phase: ① Re analysis: 20% acetonitrile
 ② Rg3 analysis: concentration gradient with 40% acetonitrile and 60% acetonitrile for 40 minutes.

Figure 2:
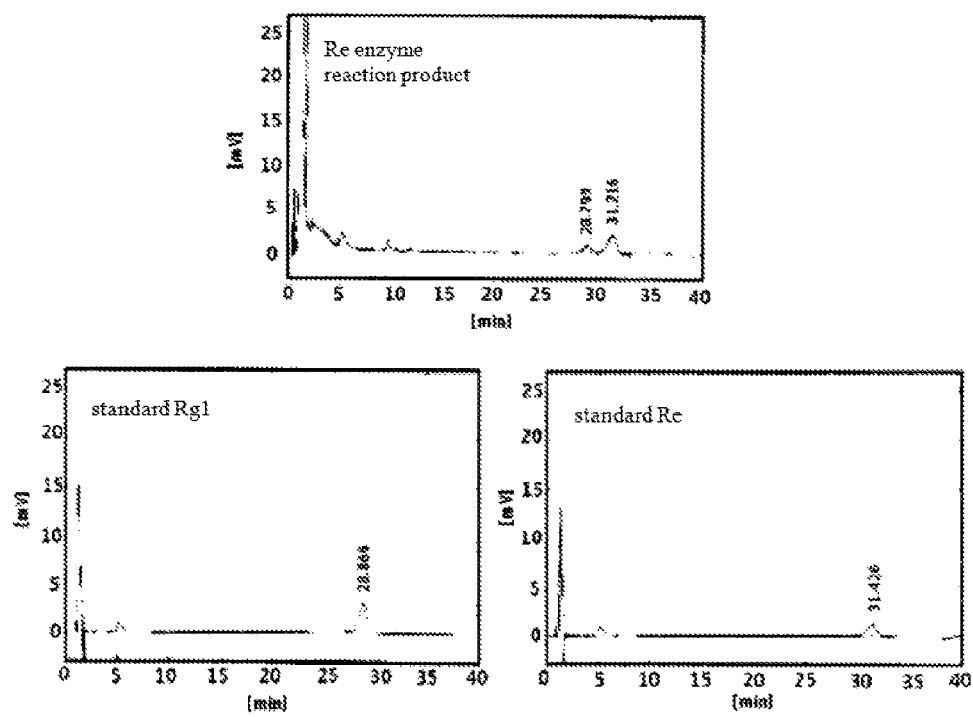
FIG. 2 is a spectrum showing that Rg1 is produced when the standard Re is reacted with the enzyme of the present invention, thereby producing α-rhamnosidase.
Figure 3:
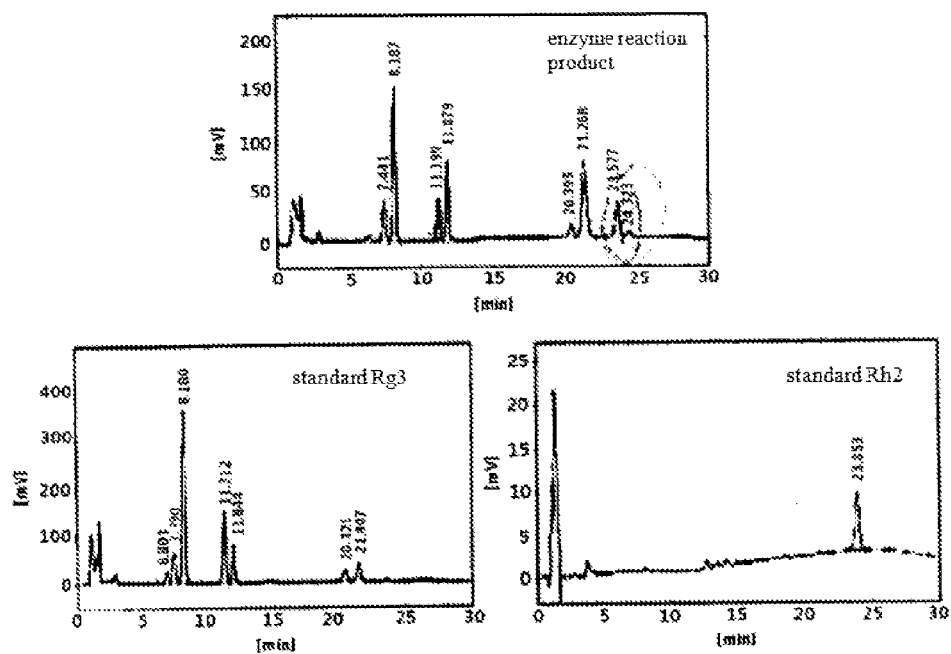
FIG. 3 is a spectrum showing that Rh2 is produced when the standard Rg3 is reacted with the enzyme of the present invention, thereby producing β-glucosidase.

From the test results, it could be seen that, when the standard Re was reacted with the enzyme of the present invention, Rg1 was produced, suggesting that α-rhamnosidase is present in the saponinase of the present invention. In addition, it could be seen that, when the standard Rg3 was reacted with the enzyme of the present invention, Rh2 was produced, suggesting that beta-glucosidase is present in the saponinase of the present invention (FIGS. 2 and 3).

Test Example 2

TLC Analysis of Saponinase

Figure 4:
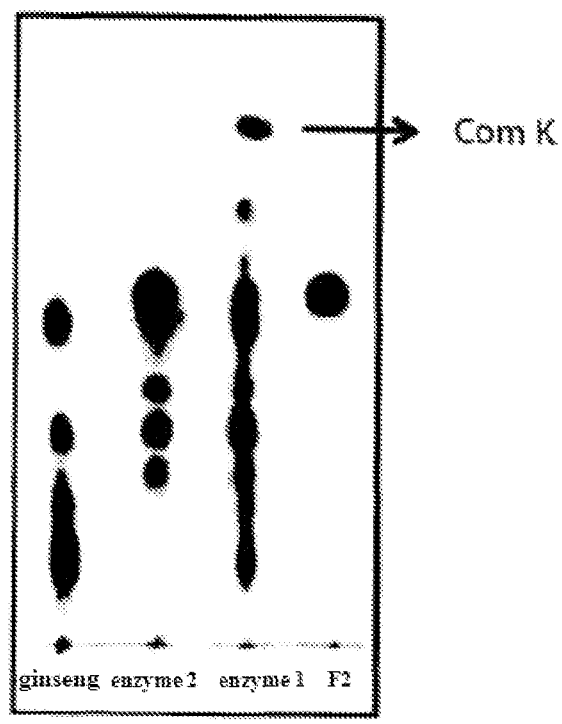
FIG. 4 is a thin film chromatograph (TLC) showing the activities of enzyme 2 passed through an ultrafiltration membrane in steps (c) and (d) of the present invention and enzyme 1 not passed through an ultrafiltration membrane.
Figure 5:
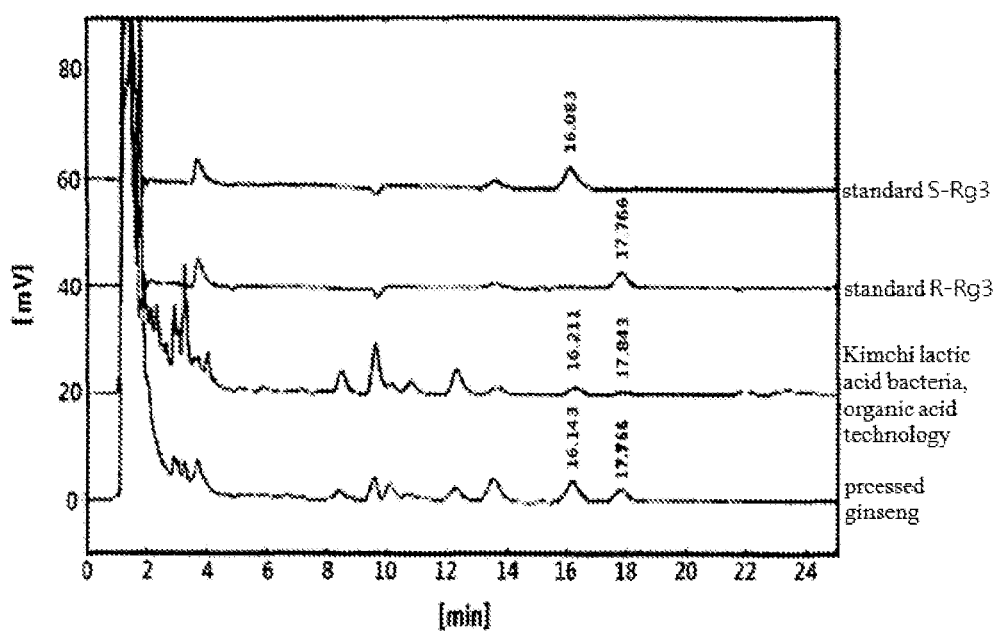
FIG. 5 is a spectrum showing a comparison of the production of Rg3 between the present invention and the prior art.
Figure 6:
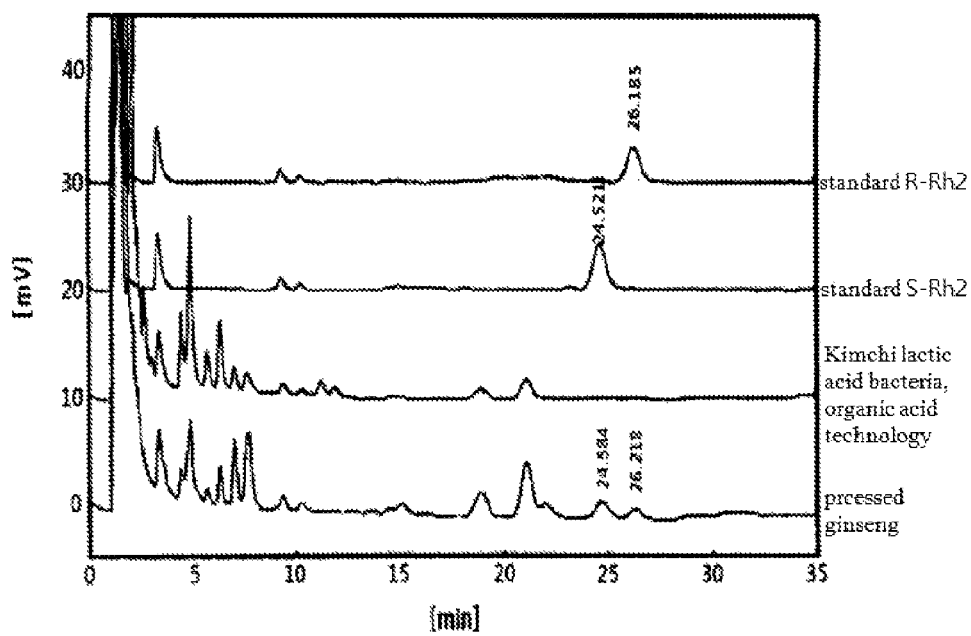
FIG. 6 is a spectrum showing a comparison of the production of Rh2 between the present invention and the prior art.

Saponinase was cultured and passed through an ultrafiltration membrane to obtain enzyme 2. 25 mg of each of enzyme 2 and enzyme 1 not passed through an ultrafiltration membrane was reacted with 50 mg of the standard Rb1, and the reaction products were analyzed by TLC. In the TLC analysis, $CHCl_3$:MeOH:$H_2O$=7:2.5:0.5 was used as a developing solution, and 5% sulfuric acid-anisaldehyde solution was used as a color developing reagent (FIG. 4).

Test Example 3

Determination of Ratio of Saponinases

The saponinase of the present invention was added slowly to ammonium sulfate in an amount of 50% (w/v) at 4° C. while the mixture was well stirred. The enzyme solution was centrifuged at 12000×G for 30 minutes, and the precipitate was collected, dissolved in 0.01M sodium acetate buffer solution and dialyzed in the same buffer solution. The dialyzed enzyme solution was passed through a DEAE-cellulose column so that it was adsorbed onto the column, and 0.01 mol of potassium chloride was added thereto so that the enzyme was separated into fractions. Among the separated enzyme fractions, only fractions having enzymatic activity were confirmed to obtain relatively purified beta-glucosidase and alpha-rhamnosidase, and the ratio of the obtained beta-glucosidase and alpha-rhamnosidase were determined (see Table 2).

TABLE 2

Ratio of relatively purified beta-glucosidase and alpha-rhamnosidase

| | Yield (wt %) | | Weight ratio (beta-glucosidase:alpha-rhamnosidase) |
|---|---|---|---|
| | beta-glucosidase | alpha-rhamnosidase | |
| First | 8.4 | 2.8 | 3.0:1 |
| Second | 25 | 3.2 | 7.8:1 |
| Third | 12 | 25 | 4.8:1 |

Test Example 4

Acute Toxicity Test

The processed ginseng concentrate obtained in Example was dissolved in purified water at concentrations of 100, 300 and 500 mg/mL to obtain sample solutions for administration to mice. 6-week-old healthy male and female healthy ICR mice were fasted for 5 hours before administration of the sample solutions, and then 10 mL/kg of each sample solution was administered orally to the animal groups, each consisting of 5 male mice and 5 female mice, such that the dose of the sample was 0.5 g/kg, 1 g/kg or 2 g/kg. As a control, the sample amount of purified water was administered. During the test period, the test animals were allowed access to feed and water ad libitum. For all the test animals, clinical conditions were observed continuously for 30 minutes immediately after administration of the sample solutions and observed once a day during the test period, and the bodyweights of the animals were measured immediately before administration and at 1, 3, 7 and 14 days after administration. The difference in bodyweight between the control group and the test groups was analyzed using Student's t-test.

None of the animals was killed during the test period, suggesting that the 50% lethal dose ($LD_{50}$) of the processed ginseng extract for the white mice is larger than 2 g/kg. Also, the groups administered with the sample did not show conditions thought to be caused by administration of the sample, unlike the control group, and did not show a difference in bodyweight from the control group. In addition, in autopsy after the observation period, abnormalities in the organs were not visually observed. Taking the above results together, it can be concluded that the processed ginseng or red ginseng according to the present invention is highly safe.

Test Example 5

Preparation and Effect of Anticancer Supplement Composition

As test animals, 6-week-old female Balb/c-nu/nu mice (weight: 20±2 g) supplied from Orient Co. Ltd. Were housed in a chamber at a temperature of 23±1° C. at a relative humidity of 55±15% with a 12-hr light/12-hr dark cycle. The animals were acclimated for 1 week while these were allowed access to feed (Orient Co. Ltd.) ad libitum, and then conditions in the animals were visually observed. After acclimatization for 1 week, 100 µl of HT-29 cells were transplanted subcutaneously into the flank of the Balb/c nu/nu mouse at a concentration of $1 \times 10^7$ cells/mouse, followed by visual observation. The mice having a tumor size of about 200 mm³ were randomly grouped, and then administration of the drug sample was initiated. The weight and the tumor volume were measured twice a week, and the measurement of the tumor volume was performed by measuring the tumor length and width using Vernier calipers. The tumor volume was calculated using the following equation:

*Tumor volume (mm³)=$l \times w^2 \times 0.5$ wherein l=length, and w=width.

Each of the ginseng products prepared in the above Examples and Comparative Examples and various ginseng-related concentrates was diluted in distilled water (DW) at a concentration of 100 mg/kg BW, and then administered orally to the mice using an oral sonde. The test sample was administered at a dose of 200 µl to 20 g depending on the weight measured on the day of administration, and administration of the test sample was carried out at 11 AM once a day. In FOLFOX administration, the test sample was dissolved in 3 ml of 0.9% NaCl solution at a concentration of 5-fluorouracil (5-FU)/leucovorin (LV)+Oxaliplatin (Ox)= 16:5:1 mg/kg BW, and then administered intra-abdominally once a day and five times a week. Table 3 below shows the administration methods and doses in the FOLFOX and Comparative Examples.

TABLE 3

Administration methods and doses in FOLFOX and Comparative Examples

| Test groups | Administration methods | |
| --- | --- | --- |
| Control (HT-29 cells only) | 0.9% NaCl/abdominal administration | DW/oral administration |
| FOLFOX (16:5:1 mg/kg/BW) | FOLFOX Abdominal administration (first 5 days) | DW/oral administration |
| FOLFOX + Example 2 (100 mg/kg BW) | | Oral administration (every day) of extracts of Examples |
| FOLFOX + Example 3 (100 mg/kg BW) | | |
| FOLFOX + Example 6 (100 mg/kg BW) | | |
| FOLFOX + Comparative Example 2 (100 mg/kg BW) | | |
| FOLFOX + ginseng concentrate (100 mg/kg BW) | | |
| FOLFOX + ginseng concentrate powder (100 mg/kg BW) | | |

TABLE 3-continued

Administration methods and doses in FOLFOX and Comparative Examples

| Test groups | Administration methods |
| --- | --- |
| FOLFOX + red ginseng concentrate powder (100 mg/kg BW) | |

Before sacrifice of the mice, blood was collected from the venous plexus using a heparinized capillary (Chase instruments Co.) and taken into a test tube (Sherwood medical Co.) containing EDTA(K3) and mixed using a roll mixer. Then, the levels of WBC (white blood cell), RBC (red blood cell), PLT (platelet) in the blood sample were measured using a Coulter counter. The Coulter counter was used in the blood analysis after correcting the WBC, RBC and PLT values with 4 C plus solution according to a standard solution. Also, the blood collected from the heart was immediately centrifuged at 3,000 rpm at 4° C. for 10 minutes to obtain serum. Using the collected serum, AST (aspartate aminotransferase), ALT (alanine aminotransferase), blood urea nitrogen and creatinine were quantified within 24 hours after collection of the serum. Table 4 below shows the synergistic anticancer effect of the processed ginseng extract of the present invention when used in combination with FOLFOX in Balb/C nude mice transplanted with HT-29 colorectal cancer cells. As can be seen in Table 4, when FOLFOX and the processed ginseng extract of the present invention were administered to the Balb/C nude mice transplanted with HT-29 colorectal cancer cells, a synergistic anticancer effect appeared. With respect to treatment with FOLFOX (5-Fu/LV+Ox=16:5:1 mg/kg BW), when tumor volume reached 200 mm³ after transplantation of cells, the mice were randomly grouped and FOLFOX was intra-abdominally administered to the mice continuously for the first 5 days. The drug was administered orally every day at a concentration of 100 mg/kg BW. After administration for 4 weeks, the FOLFOX group showed a cancer growth inhibition ratio of 42.7% compared to the control group. On the other hand, the administration of Example 2 in combination with FOLFOX showed a cancer growth inhibition ratio of 74.6%, and the administration of Example 3 in combination with FOLFOX showed a cancer growth inhibition ratio of 80.2%, and the administration of Example 6 in combination with FOLFOX showed a cancer growth inhibition ratio of 77%. Thus, the ginseng extracts of the Examples of the present invention showed significantly excellent anticancer effects compared to conventional ginseng concentrate, ginseng concentrate powder or red ginseng concentrate power and Comparative Example 2 (inhibition of 58.7%).

TABLE 4

Synergistic anticancer effect in the use of FOLFOX in combination with processed ginseng extract of the preset invention

| Test groups (n = 5) | Tumor volume (mm³) | Inhibition ratio (%) |
| --- | --- | --- |
| Control (HT-29 cells only) | 1960.4 ± 98.69 | 0 |
| FOLFOX (16:5:1 mg/kg/BW) | 1123.2 ± 75.19 | 42.7 |

TABLE 4-continued

Synergistic anticancer effect in the use of FOLFOX in combination with processed ginseng extract of the preset invention

| Test groups (n = 5) | Tumor volume (mm³) | Inhibition ratio (%) |
|---|---|---|
| FOLFOX + Example 2 (100 mg/kg BW) | 501 ± 27.21* | 74.6 |
| FOLFOX + Example 3 (100 mg/kg BW) | 387.2 ± 21.57* | 80.2 |
| FOLFOX + Example 6 (100 mg/kg BW) | 450.2 ± 13.8* | 77.0 |
| FOLFOX + Comparative Example 2 (100mg/kg BW) | 809.2 ± 14.22 | 58.7 |
| FOLFOX + ginseng concentrate (100 mg/kg BW) | 1124.4 ± 78.47 | 42.6 |
| FOLFOX + ginseng concentrate powder (100 mg/kg BW) | 1028.6 ± 21.83 | 47.5 |
| FOLFOX + red ginseng concentrate powder (100 mg/kg BW) | 913.8 ± 23.18 | 53.4 |

*$P < 0.01$: statistically significant compared to FOLFOX + Comparative Example 2

Table 5 below shows the results of biochemical analysis of blood obtained when FOLFOX and the processed ginseng extract were administered into the Balb/C nude mice transplanted with HT-29 colorectal cancer cells. In this test, the drug was administered to the mice for 4 weeks, followed by biochemical analysis. As a result, it could be seen that the group administered with FOLFOX showed significant decreases in WBC, RBC and PLT compared to the control group. On the contrary, in the group administered with FOLFOX in combination with the ginseng extract of the Example of the present invention, the hematological values reduced by FOLFOX were increased. Thus, the ginseng extracts of the Examples of the present invention showed high hematological values compared to conventional ginseng concentrate, ginseng concentrate powder or red ginseng concentrate power and Comparative Example 2.

TABLE 5

Results of biochemical analysis of blood obtained when FOLFOX and processed ginseng extract were used in combination

| Test groups (n = 5) | WBC (10³/μl) | RBC (10³/μl) | PLT (10³/μl) |
|---|---|---|---|
| Control (HT-29 cells only) | 17.0 ± 0.69 | 11.4 ± 0.41 | 1565.8 ± 42.67 |
| FOLFOX (16:5:1 mg/kg/BW) | 7.0 ± 0.3 | 5.7 ± 0.38 | 934.9 ± 33.16 |
| FOLFOX + Example 2 (100 mg/kg BW) | 10.9 ± 0.39 | 8.1 ± 0.38 | 1253.6 ± 62.49 |
| FOLFOX + Example 3 (100 mg/kg BW) | 13.9 ± 0.4* | 10.5 ± 0.5* | 1392.5 ± 63.36** |
| FOLFOX + Example 6 (100 mg/kg BW) | 13.1 ± 0.51* | 9.4 ± 0.46* | 1352.5 ± 52.04** |
| FOLFOX + Comparative Example 2 (100 mg/kg BW) | 9.4 ± 0.26 | 7.2 ± 0.37 | 1142.9 ± 68.01 |
| FOLFOX + ginseng concentrate (100 mg/kg BW) | 7.9 ± 0.18 | 5.9 ± 0.24 | 991.9 ± 19.8 |
| FOLFOX + ginseng concentrate powder (100 mg/kg BW) | 7.8 ± 0.37 | 6.6 ± 0.21 | 1012.6 ± 12.05 |
| FOLFOX + red ginseng concentrate powder (100 mg/kg BW) | 8.8 ± 0.38 | 6.8 ± 0.18 | 1040.7 ± 29.22 |

*$P < 0.01$,
**$P < 0.05$: statistically significant compared to FOLFOX + Comparative Example 2

Table 6 below shows the results of analyzing the changes in kidney toxicity and liver toxicity when FOLFOX and the processed ginseng extract were administered into the Balb/C nude mice transplanted with HT-29 colorectal cancer cells. In this test, the drug was administered to the mice for 4 weeks, followed by analysis of BUN (blood urea nitrogen), an index for evaluating kidney function, creatinine, and AST and ALT, indices for evaluating liver toxicity. As a result, it could be seen that, in the FOLFOX group, BUN, creatinine, AST and ALT all significantly increased compared to those in the control group, suggesting that kidney toxicity and liver toxicity significantly increased. On the contrary, in the groups administered with FOLFOX in combination with the ginseng extract of the Example of the present invention, the kidney toxicity and liver toxicity values that increased by FOLFOX were significantly reduced. Thus, the ginseng extracts of the Examples of the present invention significantly reduced kidney toxicity and liver toxicity compared to conventional ginseng concentrate, ginseng concentrate powder or red ginseng concentrate power and Comparative Example 2.

TABLE 6

Results of analysis of changes in kidney toxicity and liver toxicity when FOLFOX and processed ginseng extract were used in combination

| Test groups (n = 5) | BUN (mg/dl) | Creatinine (mg/dl) | AST (U/l) | ALT (U/l) |
|---|---|---|---|---|
| Control (HT-29 cells only) | 5.62 ± 0.27 | 5.56 ± 0.26 | 33.98 ± 0.94 | 8.10 ± 0.46 |
| FOLFOX (16:5:1 mg/kg/BW) | 57.14 ± 2.30 | 15.94 ± 0.85 | 97.98 ± 4.11 | 27.18 ± 1.85 |
| FOLFOX + Example 2 (100 mg/kg BW) | 39.48 ± 1.54 | 12.12 ± 0.58 | 56.58 ± 1.79 | 19.32 ± 1.38 |
| FOLFOX + Example 3 (100 mg/kg BW) | 26.36 ± 1.28* | 8.54 ± 0.55* | 40.04 ± 1.88* | 15.48 ± 0.78* |
| FOLFOX + Example 6 (100 mg/kg BW) | 33.08 ± 1.51* | 12.68 ± 0.81 | 55.68 ± 1.48 | 20.98 ± 1.55 |
| FOLFOX + Comparative Example 2 (100 mg/kg BW) | 42.42 ± 1.70 | 13.60 ± 0.77 | 63.50 ± 4.24 | 21.90 ± 1.04 |

TABLE 6-continued

Results of analysis of changes in kidney toxicity
and liver toxicity when FOLFOX and processed
ginseng extract were used in combination

| Test groups (n = 5) | BUN (mg/dl) | Creatinine (mg/dl) | AST (U/l) | ALT (U/l) |
|---|---|---|---|---|
| FOLFOX + ginseng concentrate (100 mg/kg BW) | 52.64 ± 2.36 | 15.66 ± 0.40 | 93.06 ± 3.24 | 26.34 ± 1.88 |
| FOLFOX + ginseng concentrate powder (100 mg/kg BW) | 54.10 ± 3.33 | 15.72 ± 0.35 | 94.10 ± 3.98 | 24.30 ± 1.90 |
| FOLFOX + red ginseng concentrate powder (100 mg/kg BW) | 46.66 ± 1.86 | 15.38 ± 0.39 | 90.66 ± 6.08 | 26.38 ± 1.88 |

*$P < 0.01$: statistically significant compared to FOLFOX + Comparative Example 2

INDUSTRIAL APPLICABILITY

The pharmacological effects of ginseng were found by many studies, various ginseng processing technologies and ginseng fermentation technologies, which are not simple extraction or processing methods, have been developed since 2000. Despite the development of such various technologies, high-value-added ginseng products are not being produced. This is because there is an efficiency-associated problem in mass production and a standardized production method is not established. Pharmaton (Boehringer Ingelheim, Germany) that is a typical ginseng product is a product produced by a simple ginseng extraction process, but the annual sales value thereof is more than 500 billion dollars. This is because Pharmaton is produced by a standardized production process so as to have constant ginsenoside contents. Thus, a standardized production process for a ginseng product is very important, and the present invention provides method of preparing a processed ginseng or processed ginseng extract having increased contents of ginsenosides Rg3 and Rh2 by a standardized production process. In addition, the present invention provides an anticancer supplement composition comprising the processed ginseng or processed ginseng extract prepared by the method of the present invention and can be applied to the development of high-value-added ginseng products.

The invention claimed is:

1. A method for preparing a processed ginseng or processed ginseng extract having increased contents of ginsenosides Rg3 and Rh2, the method comprising the steps of:
   (a) inoculating an *Aspergillus niger* strain into a medium composed of ginseng and wheat bran;
   (b) culturing the strain of step (a) to produce a cultured material;
   (c) purifying the cultured material of step (b) by ultrafiltration to produce a purified material using a membrane having a cutoff molecular weight of 100 KDa;
   (d) separating an enzyme from the purified material of step (c), wherein the enzyme comprises β-glucosidase and α-rhamnosidase;
   (e) adding the enzyme of step (d) to ginseng, red ginseng or a ginseng or red ginseng extract to obtain a mixture;
   (f) fermenting the mixture of step (e) to produce a fermented material;
   (g) separating the fermented material of step (f) to obtain a supernatant;
   (h) concentrating the supernatant of step (g) to produce a concentrate;
   (i) reacting the concentrate of step (h) with at least one organic acid selected from the group consisting of acetic acid, lactic acid, citric acid, malic acid and tartaric acid to produce a reaction product; and
   (j) neutralizing, filtering, purifying, concentrating and drying the reaction product of step (i).

2. The method of claim 1, wherein inoculation of the medium with *Aspergillus niger* in step (a) is performed, wherein the number of spores in an *Aspergillus niger* spore suspension is $5 \times 10^5$ spores per g of the medium and initial water content of the medium is maintained at 50-80%.

3. The method of claim 1, wherein the β-glucosidase and α-rhamnosidase are present at a ratio (g/g) of 3:1 to 8:1.

4. The method of claim 1, wherein the addition of the enzyme in step (e) is performed by adding the enzyme of step (d) in an amount of 5-20% based on the weight of the ginseng, the red ginseng or the ginseng or red ginseng extract.

5. The method of claim 1, wherein the organic acid in step (i) is added to a 10% solution of the concentrate of step (h) in purified water in an amount of 1-50 wt % based on the weight of the concentrate solution, and the reaction in step (i) is carried out at a temperature of 40~80° C. for 2-18 hours.

6. The method of claim 1, wherein the fermentation in step (f) is carried out at a temperature of 25~60° C. for 6-24 hours.

* * * * *